(12) United States Patent
Kanyuh

(10) Patent No.: US 8,735,642 B2
(45) Date of Patent: May 27, 2014

(54) TWO STAGE CONTACT COOLER DESIGN FOR HOT WATER GENERATION

(75) Inventor: Adam Kanyuh, Streamwood, IL (US)

(73) Assignee: UOP LLC, Des Plaines, IL (US)

(*) Notice: Subject to any disclaimer, the term of this patent is extended or adjusted under 35 U.S.C. 154(b) by 995 days.

(21) Appl. No.: 12/165,103

(22) Filed: Jun. 30, 2008

(65) Prior Publication Data

US 2009/0326301 A1   Dec. 31, 2009

(51) Int. Cl.
*C07C 4/06* (2006.01)

(52) U.S. Cl.
USPC ........... 585/648; 585/650; 585/651; 585/653; 585/833; 585/834; 585/910

(58) Field of Classification Search
USPC ......... 585/648, 652, 649, 650, 651, 653, 833, 585/834, 910; 261/148, 151
See application file for complete search history.

(56) References Cited

U.S. PATENT DOCUMENTS

| | | | |
|---|---|---|---|
| 3,597,494 A * | 8/1971 | Bigache et al. | 585/652 |
| 3,674,890 A * | 7/1972 | Oleszko et al. | 585/535 |
| 4,279,734 A | 7/1981 | Gwyn | |
| 5,071,627 A | 12/1991 | Child et al. | |
| 6,121,504 A | 9/2000 | Kuechler et al. | |
| 6,312,503 B1 * | 11/2001 | Fike et al. | 95/211 |
| 6,403,854 B1 * | 6/2002 | Miller et al. | 585/638 |
| 6,482,998 B1 | 11/2002 | Kuechler et al. | |
| 6,740,791 B2 | 5/2004 | Kuechler et al. | |
| 7,038,102 B2 | 5/2006 | Van Egmond et al. | |
| 7,087,155 B1 * | 8/2006 | Dath et al. | 208/118 |
| 7,235,172 B2 | 6/2007 | Lawson et al. | |
| 7,288,692 B2 | 10/2007 | Kuechler et al. | |
| 7,361,799 B2 | 4/2008 | Kuechler et al. | |
| 2004/0069684 A1 * | 4/2004 | Tallman et al. | 208/161 |
| 2005/0033098 A1 | 2/2005 | Sumner et al. | |
| 2005/0065390 A1 | 3/2005 | Van Egmond et al. | |
| 2007/0055087 A1 | 3/2007 | Powers | |
| 2007/0208207 A1 | 9/2007 | Powers | |

FOREIGN PATENT DOCUMENTS

JP  3008679 B4  2/1991

OTHER PUBLICATIONS

Fair, et al., "Gas Absorption and Gas-Liquid System Design" in Perry's Chemical Engineer's Handbook, 7th ed., R. H. Perry, ed., McGraw-Hill (1997) available on-line at www.knovel.com.*
Lide, et al., CRC Handbook of Chemistry and Physics, 91st ed., 2011 Internet edition.*

(Continued)

*Primary Examiner* — In Suk Bullock
*Assistant Examiner* — Bradley Etherton
(74) *Attorney, Agent, or Firm* — Arthur E Gooding

(57) ABSTRACT

Systems and methods are provided herein for cooling an olefin cracking reactor effluent stream. One provided method includes reacting a hydrocarbon feedstock including $C_4+$ olefins in an olefin cracking reactor to produce an olefin cracking reactor effluent stream, providing the olefin cracking reactor effluent stream to an inlet of a contact cooler, contacting the olefin cracking reactor effluent stream with a first quench liquid in a first contact zone in the contact cooler to produce a first bottoms stream and an intermediate vapor stream, contacting the intermediate vapor stream with a second quench liquid in a second contact zone in the contact cooler to produce a second bottoms stream and a cooled vapor stream, and removing the cooled vapor stream from an outlet of the contact cooler. The method can also include cooling the first bottoms stream to provide a cooled first bottoms stream, and cooling the second bottoms stream to provide a cooled second bottoms stream.

15 Claims, 1 Drawing Sheet

(56) References Cited

OTHER PUBLICATIONS

Shilling, et al., "Heat Transfer Equipment" in Perry's Chemical Engineer's Handbook, 7th ed., R. H. Perry, ed., McGraw-Hill (1997) available on-line at www.knovel.com.*

Speight, Lange's Handbook of Chemistry, J. G. Speight, ed., 16th ed., McGraw-Hill, 2005, available on-line at www.knovel.com—month unknown.*

Sundaram, et al., "Ethylene" in Kirk-Othmer Encyclopedia of Chemical Technology, J. Wiley and Sons, available on-line Apr. 16, 2001.*

* cited by examiner

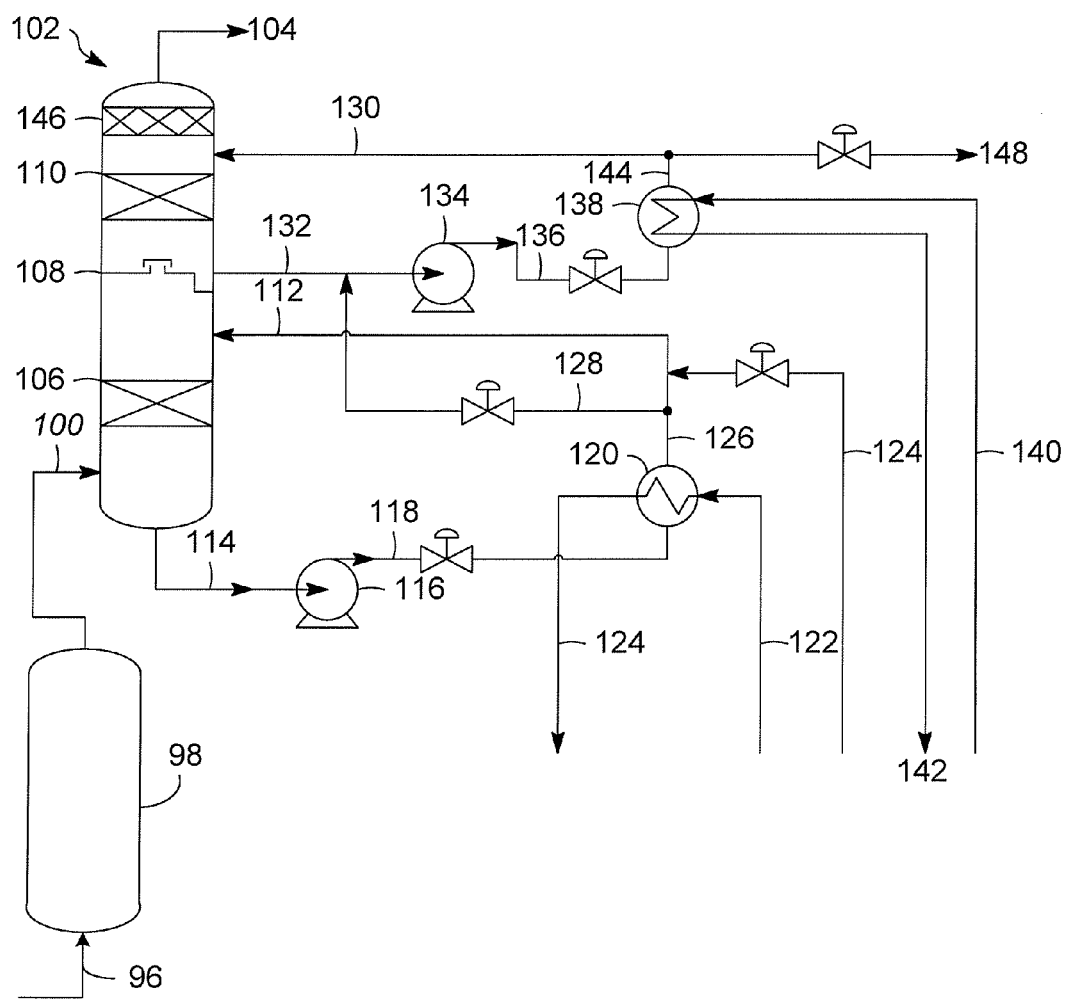

TWO STAGE CONTACT COOLER DESIGN FOR HOT WATER GENERATION

TECHNICAL FIELD

This disclosure relates to the production of light olefins and, more particularly, to the production of light olefins via the cracking of heavier olefins.

DESCRIPTION OF RELATED ART

Light olefins are essential building blocks for the petrochemical and chemical industries, and can be use in the production of numerous important chemical products via polymerization, oligomerization, alkylation and other well-known chemical reactions. The term "light olefins" generally refers to $C_2$ and $C_3$ olefins, i.e., ethylene and propylene.

Olefin conversion technologies may be employed to produce light olefins from olefin containing feedstocks. Such olefin conversion processes can be combined or integrated with other olefin producing technologies such as, for example, steam or fluid catalytic cracking processes or oxygenate to olefin processes, to provide increased light olefin production.

There are two primary types of olefin conversion technologies for producing light olefins, metathesis and olefin cracking. Metathesis processes typically produce propylene by reacting ethylene with 2-butenes. Olefin cracking processes typically produce ethylene and propylene by cracking or converting feed streams containing $C_4+$ olefins, such as, for example, $C_4$-$C_8$ olefin containing feedstocks, to produce effluent streams containing predominantly $C_2$-$C_6$ compounds along with some hydrogen and other lighter gases. Such effluent streams are subsequently separated into various product streams such as, for example, product streams containing ethylene and propylene.

Olefin cracking processes are generally conducted in a catalytic reactor at elevated temperatures, and typically produce effluent streams having temperatures in excess of 930° F. (500° C.). Typically, such olefin cracking reactor effluent streams are subsequently cooled and compressed to facilitate separation into individual product streams.

SUMMARY

This disclosure relates to systems and processes for cooling an olefin cracking reactor effluent stream.

In one aspect, a process for cooling an olefin cracking reactor effluent stream is provided that includes reacting a hydrocarbon feedstock including $C_4+$ olefins in an olefin cracking reactor to produce an olefin cracking reactor effluent stream and providing the olefin cracking reactor effluent stream to an inlet of a contact cooler. In the contact cooler, the olefin cracking reactor effluent stream is contacted with a first quench liquid in a first contact zone to produce a first bottoms stream and an intermediate vapor stream. The intermediate vapor stream is contacted with a second quench liquid in a second contact zone in the contact cooler to produce a second bottoms stream and a cooled vapor stream. The first quench liquid and second quench liquid can each be a quench oil. The cooled vapor stream is removed from an outlet of the contact cooler. Preferably, the intermediate vapor stream is passed through an accumulator tray prior to contacting the intermediate vapor stream with the second quench liquid in a second contact zone. The cooled vapor stream can also be through a mesh blanket before being removed from the contact cooler. Additionally, the first bottoms stream is cooled to provide a cooled first bottoms stream, and the second bottoms stream is cooled to provide a cooled second bottoms stream. A first exchanger and a second heat exchanger can be used for the cooling of the first bottoms stream and the second bottoms stream, respectively. At least a portion of the cooled first bottoms stream can be returned to the contact cooler as at least a portion of the first quench liquid. Similarly, at least a portion of the cooled second bottoms stream can be returned to the contact cooler as at least a portion of the second quench liquid.

In another aspect, a system for cooling an olefin cracking reactor effluent stream is provided that includes an olefin cracking reactor, a contact cooler, a first heat exchanger, and a second heat exchanger. The olefin cracking reactor receives a hydrocarbon feedstock including $C_4$ to $C_8$ olefins and produces an olefin cracking reactor effluent stream. The contact cooler has an inlet that receives the olefin cracking reactor effluent stream. The contact cooler also includes a first contact zone where the olefin cracking reactor effluent stream contacts a first quench liquid to produce an intermediate vapor stream and a first bottoms stream, an accumulator tray, a second contact zone where the intermediate vapor stream contacts a second quench liquid to produce a cooled vapor stream and a second bottoms stream, and an outlet through which the cooled vapor stream is removed from the contact cooler. The first heat exchanger that removes heat from the first bottoms stream by indirect heat exchange with a first cooling liquid. The second heat exchanger that removes heat from the second bottoms stream by indirect heat exchange with a second cooling liquid.

BRIEF DESCRIPTION OF THE DRAWINGS

Exemplary systems and methods have been chosen for purposes of illustration and description, and are shown in the accompanying drawings, forming a part of the specification.

FIG. 1 is a simplified schematic view of one form of a system including a contact cooler.

DETAILED DESCRIPTION

A hydrocarbon feedstock including $C_4+$ olefins, and preferably containing at least $C_4$ to $C_8$ olefins, can be reacted in an olefin cracking reactor to produce a olefin cracking reactor effluent stream. Such a feedstock can be provided by any suitable source. For example, feedstock streams containing $C_4+$ olefins can be generated by a refinery, or by a steam cracker. Feedstock streams containing $C_4+$ olefins can also be produced as byproduct streams in oxygenate to olefin (OTO) processes, such as methane to olefin (MTO) processes. Hydrocarbon olefin based feedstock containing $C_4+$ olefins that is provided to an olefin cracking reactor can be a liquid, a vapor, or a mixture thereof.

As illustrated in FIG. 1, an olefin cracking reactor 98 can receive a hydrocarbon feedstock 96 including $C_4+$ olefins and produce an olefin cracking reactor effluent stream 100. The olefin cracking reactor 98 preferably includes a fixed catalyst bed, although some forms can utilize a moving bed. Additionally, an olefin cracking reactor 98 can be oriented in an upflow configuration, a down flow configuration, or a radial flow configuration. The catalyst used in an olefin cracking reactor 98 can be any suitable catalyst. For example, in some forms the catalyst can be a crystalline silicate of the MFI family, which may be a zeolite, a silicalite or any other silicate in that family, or the MEL family which may be a zeolite or any other silicate in that family. Examples of MFI silicates include, but are not limited to, ZSM-5 and silicalite. Catalyst material can include one or binders. In some examples, a diluent, such as, for example, nitrogen, or methane can be added to the olefin cracking reactor in addition to the hydrocarbon olefin based feedstock containing $C_4+$ olefins. An olefin cracking reactor can have a reaction temperature of from about 840° F. (about 450° C.) to about 1110° F. (about 600° C.), and preferably from about 930° F. (about 500° C.) to about 1110° F. (about 600° C.). An olefin cracking reactor 98 can also have a range of suitable operating pressures. In some forms, the pressure at the outlet of an olefin cracking reactor can be from about 1 psig to about 10 psig, preferably from about 3 psig to about 7 psig, and most preferably from about 5 psig to about 7 psig.

Without being bound by any particular theory, it is believed that an olefin cracking reactor 98 having a lowered operating pressure, and thus a lower pressure at its outlet, has an increased selectivity to light olefins, and thus increased light olefin yield. For example, it is believed that a drop in the outlet pressure of an olefin cracking reactor of about 2 psig, such as from about 7 psig to about 5 psig, can result in a 2-3% increase in propylene selectivity.

Catalytic cracking of an olefin containing feedstock can be understood to comprise a process yielding at least some quantity of shorter molecules via bond breakage. For example, heavy olefins in the $C_4$ to $C_8$ range can be cracked down to produce light olefins in the $C_2$ to $C_3$ range. An olefin cracking reactor effluent stream can comprise a range of hydrocarbon products including $C_2$ and/or $C_3$ olefins, unconverted $C_4$ to $C_8+$ hydrocarbons, and aromatic hydrocarbons such as, for example, benzene and toluene, as well as some hydrogen and other light gases such as, for example, methane, ethane and/or propane.

The olefin cracking reactor effluent stream can be separated into various product streams. Preferably, the olefin cracking reactor effluent stream can be cooled prior to being separated, and the olefin cracking reactor effluent stream is preferably also compressed. Cooling of the olefin cracking reactor effluent stream can be accomplished by any suitable method, such as, for example, indirect heat exchange in a heat exchanger.

Olefin cracking reactor effluent streams can be cooled using various methods such as, for example, direct or indirect heat exchange with a cooling medium. One known indirect heat exchange method generally involves passing the hot olefin cracking reactor effluent through a heat exchange unit such as, for example, a tube and shell heat exchanger, to produce a cooled olefin cracking reactor effluent stream having a temperature profile that is suitable for efficient compression. Such indirect heat exchange units, however, can be susceptible to fouling by constituents of the olefin cracking reactor effluent stream. For example, heavy hydrocarbon compounds can condense on surfaces of the heat exchange unit, which can result in a reduction of the cooling capacity of the heat exchange unit. Generally, the temperature of a gas to be compressed controls the capacity of an associated compressor, and the higher the temperature of the gas the less it can be compressed. Thus, the reduction in the cooling capacity of the heat exchange unit results in reduced compression capacity in the associated compressor. This can result in increased down time for cleaning of the heat exchange units and decreased product output.

Additionally, gaseous materials which pass through indirect heat exchange units can also experience a significant pressure drop from the inlet of the heat exchanger to the outlet of the heat exchanger. Thus can result in a cooled effluent stream having a pressure which is lower than may be desired, and can require additional energy expenditures and increased compressor size to compress the cooled effluent stream to a pressure suitable for further processing in subsequent separation units. Further, a pressure drop across the heat exchange unit can result in an increased pressure at an associated olefin cracking reactor outlet which can cause reductions in the yield of ethylene and/or propylene produced by the olefin cracking process.

FIG. 1 illustrates a preferred system and process for cooling an olefin cracking reactor effluent stream 100 to produce a cooled vapor stream 104. Olefin cracking reactor effluent stream 100 can have a temperature of from about 250° F. (about 120° C.) to about 1110° F. (about 600° C.), preferably from about 300° F. (about 150° C.) to about 400° F. (about 210° C.). Cooled vapor stream 104 preferably has a temperature from about 75° F. (about 25° C.) to about 130° F. (about 55° C.), and can have a temperature from about 95° F. (about 35° C.) to about 115° F. (about 45° C.).

As illustrated, an olefin cracking reactor effluent stream 100 can be provided to an inlet of a contact cooler 102. Olefin cracking reactor effluent stream 100 can undergo one or more cooling steps after leaving the olefin cracking reactor and prior to entering the contact cooler 102, such as undergoing indirect heat exchange with one or more cooling streams. Olefin cracking reactor effluent stream 100 is preferably in a vapor state when it enters the contact cooler 102.

Contact cooler 102 has an inlet that receives olefin cracking reactor effluent stream 100, and an outlet from which cooled vapor stream 104 can be removed. Contact cooler 102 also includes a first contact zone 106, and a second contact zone 110. The inlet of the contact cooler is preferably located below the first contact zone. The outlet of the contact cooler is preferably above the second contact zone 110. The contact cooler 102 can have a first pressure at the inlet and a second pressure at the outlet, but it is preferred that any drop in pressure be minimized. For example, the difference between the first pressure and the second pressure can be from about 0.5 psi to about 1.0 psi, and is preferably less than about 1.0 psi.

In the first contact zone 106 of the contact cooler 102, the olefin cracking reactor effluent stream 100 is contacted with a first quench liquid 112 to produce a first bottoms stream and an intermediate vapor stream. The first quench liquid 112 can be introduced into the contact cooler 102 above the first contact zone 106. The olefin cracking reactor effluent stream 100 preferably contacts the first quench liquid 112 in the first contact zone 106 in a countercurrent manner, to produce the first bottoms stream 114 and the intermediate vapor stream.

The intermediate vapor stream can be provided to a second contact zone 110. In the second contact zone 110, the intermediate vapor stream can be contacted with a second quench liquid 130 to produce a second bottoms stream 132 and a cooled vapor stream 104. The second quench liquid 130 can be introduced into the contact cooler 102 above the second contact zone 110. The intermediate vapor stream preferably contacts the second quench liquid 130 in the second contact zone 110 in a countercurrent manner, to produce the second bottoms stream 132 and the cooled vapor stream 104. In one form, the intermediate vapor stream can be passed through an accumulator tray 108 prior to being contacted with the second quench liquid in the second contact zone 110.

The cooled vapor stream 104 can be removed from an outlet in the contact cooler 102. In one form, the cooled vapor stream 104 can be passed through a mesh blanket or wire scrubber 146 before being removed from the contact cooler 102. The mesh blanket or wire scrubber 146 can be constructed of tightly wrapped wires composed of an inert and/or corrosion-resistant material such as, for example, 316 stainless steel. As the cooled vapor stream 104 passes through the mesh blanket or wire scrubber 102, liquid droplets can be removed from the cooled vapor stream 104. Such liquid droplets can contain condensed hydrocarbons such as, for example, $C_6+$ hydrocarbons, and/or aromatic compounds such as, for example, benzene and toluene. The liquid droplets can be collected and removed from the contact cooler 102 as part of the second bottoms stream 132.

The first and second contact zones 106 and 110 can each include a packed bed. A packed bed included in a contact zone can include an inert packing material. Inert packing material can be random, such as, for example, Racshig rings, or can be structured, such as, for example, wire mesh. Alternatively, a contact zone can include a tray assembly, such as for example, a disk and doughnut tray assembly. In some applications, a contact zone including a combination of a packed bed and a tray assembly can be utilized.

The first and second quench liquids 112 and 130 can each be a quench oil. Quench oil suitable for use as either the first quench liquid 112 of the second quench liquid 130 can include, for example, at least one $C_{10}+$ hydrocarbon material. The use of such $C_{10}+$ hydrocarbon materials is preferred to minimize or prevent vaporization of the quench liquid material into the intermediate vapor stream or the cooled vapor stream. Quench oils suitable for use as either the first or second quench liquid include, but are not limited to light cycle oils and kerosene.

When contacted with the olefin cracking reactor effluent stream 100 in the first contact zone 106, the first quench liquid 112 can cause heavier components of the olefin cracking reactor effluent stream 100 and to condense and become part of the first bottoms stream 114. Similarly, when contacted with the intermediate vapor stream in the second contact zone 110, the second quench liquid 112 can cause heavier components of the intermediate vapor stream to condense and become part of the second bottoms stream 132. Accordingly, the first and second bottoms streams 114 and 132 can each include $C_6+$ hydrocarbons, and/or aromatic compounds such as, for example, benzene and toluene.

The first bottoms stream 114 can be cooled, and can be utilized in a first pump around stream 118. The first bottoms stream 114 can have a temperature of from about from about 180° F. (about 80° C.) to about 380° F. (about 195° C.), or from about 190° F. (about 80° C.) to about 200° F. (about 95° C.). The first bottoms stream 114 can be cooled by any suitable method to provide a cooled first bottoms stream. For example, as illustrated in FIG. 1, first bottoms stream 114 can be removed from the contact cooler 102 and pumped by pump 116 as first pump around stream 118 to a heat exchanger 120, to be cooled by indirect heat exchange with a first cooling liquid 122. First cooling liquid 122 can be a first water stream. The first cooling liquid 122 can have any temperature suitable for acting as a cooling liquid, and can be, for example, from about 100° F. (about 40° C.) to about 200° F. (about 95° C.), or from about 140° F. (about 60° C.) to about 180° F. (about 80° C.). Upon undergoing heat exchange in heat exchanger 120, the first bottoms stream can be cooled, producing cooled first bottoms stream 126. Cooled first bottoms stream 126 can have a temperature of from about from about 70° F. (about 20° C.) to about 100° F. (about 40° C.), or from about 95° F. (about 35° C.) to about 100° F. (about 40° C.). At least a portion of the cooled first bottoms stream 126 can be returned to the contact cooler 102 as at least a portion of the first quench liquid 112. Optionally, additional quench liquid 124 can be combined with the portion of bottoms stream 126 to be provided as first quench liquid 112.

The second bottoms stream 132 can be cooled, and can be utilized in a second pump around stream 136. The second bottoms stream 132 can have a temperature of from about from about 100° F. (about 40° C.) to about 120° F. (about 50° C.), or from about 100° F. (about 40° C.) to about 110° F. (about 45° C.). The second bottoms stream 132 can be cooled by any suitable method to provide a cooled second bottoms stream. For example, as illustrated in FIG. 1, second bottoms stream 132 can be removed from the contact cooler 102 and pumped by pump 134 as first pump around stream 136 to a heat exchanger 138, to be cooled by indirect heat exchange with a second cooling liquid 140. Second cooling liquid 140 can be a second water stream. The second cooling liquid 140 can have any temperature suitable for acting as a cooling liquid, and can be, for example, from about 60° F. (about 15° C.) to about 100° F. (about 40° C.), or from about 80° F. (about 25° C.) to about 90° F. (about 30° C.). Upon undergoing heat exchange in heat exchanger 138, the second bottoms stream can be cooled, producing cooled second bottoms stream 144. Cooled second bottoms stream 144 can have a temperature of from about from about 70° F. (about 20° C.) to about 115° F. (about 45° C.), or from about 95° F. (about 35° C.) to about 115° F. (about 45° C.). At least a portion of the cooled first bottoms stream 144 can be returned to the contact cooler 102 as at least a portion of the second quench liquid 130. Optionally, at least a portion of the cooled first bottoms stream 126 can be combined with the second bottoms stream 132 in the second pump around stream 136, to become a portion of the cooled second bottoms stream 144.

A portion of the cooled second bottoms stream 144 be removed from or drawn off to produce a drag oil stream 148. Utilization of drag stream 148 can reduce or eliminate the build-up of heavy hydrocarbons such as, for example, $C_6+$ hydrocarbons, and/or aromatic hydrocarbons such as, for example, benzene and toluene, which are absorbed or extracted from the olefin cracking reactor effluent stream 100 and the intermediate vapor stream in the contact cooler 102.

From the foregoing, it will be appreciated that although specific forms of systems and methods have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the subject matter this disclosure.

What is claimed is:

1. A process for cooling an olefin cracking reactor effluent stream, the process comprising:
reacting a hydrocarbon feedstock including $C_4+$ olefins in an olefin cracking reactor, wherein the reactor is operated at a pressure from about 5 psig to 7 psig, to produce an olefin cracking reactor effluent stream;
providing the olefin cracking reactor effluent stream to an inlet of a contact cooler;
contacting the olefin cracking reactor effluent stream with a first quench liquid in a first contact zone in the contact cooler to produce a first bottoms stream and an intermediate vapor stream;
cooling the first bottoms stream to provide a cooled first bottoms stream;
contacting the intermediate vapor stream with a second quench liquid in a second contact zone in the contact cooler to produce a second bottoms stream and a cooled vapor stream;

cooling the second bottoms stream to provide a cooled second bottoms stream;

removing the cooled vapor stream from an outlet of the contact cooler; and passing the cooled vapor stream through a mesh blanket before removing the cooled vapor stream from the contact cooler; wherein the first quench liquid and the second quench liquid each comprise at least one $C_{10}+$ hydrocarbon to minimize vaporization of the quench liquid, and wherein the first and second contact zones each comprise a packed bed.

2. The process of claim 1, further comprising:

passing the intermediate vapor stream through an accumulator tray prior to contacting the intermediate vapor stream with the second quench liquid in a second contact zone.

3. The process of claim 1, further comprising:

returning at least a portion of the cooled first bottoms stream to the contact cooler as at least a portion of the first quench liquid; and returning at least a portion of the cooled second bottoms stream to the contact cooler as at least a portion of the second quench liquid.

4. The process of claim 1, wherein the first bottoms stream is cooled by heat exchange with a first water stream.

5. The process of claim 1, wherein the second bottoms stream is cooled by heat exchange with a second water stream.

6. The process of claim 1, wherein the cooled vapor stream has a temperature of from about 75° F. to about 130° F.

7. The process of claim 1, wherein the contact cooler has a first pressure at the inlet and a second pressure at the outlet, and difference between the first pressure and the second pressure is from about 0.5 psi to about 1.0 psi.

8. A process for cooling an olefin cracking reactor effluent stream, the process comprising:

reacting a hydrocarbon feedstock including $C_4+$ olefins in an olefin cracking reactor, wherein the reactor is operated at a pressure from about 5 psig to about 7 psig, to produce an olefin cracking reactor effluent stream;

providing the olefin cracking reactor effluent stream to an inlet of a contact cooler;

contacting the olefin cracking reactor effluent stream with a first quench oil in a first contact zone in the contact cooler to produce a first bottoms stream and an intermediate vapor stream;

cooling the first bottoms stream in a heat exchanger to provide a cooled first bottoms stream;

passing the intermediate vapor stream through an accumulator tray to a second contact zone;

contacting the intermediate vapor stream with a second quench oil in the second contact zone in the contact cooler to produce a second bottoms stream and a cooled vapor stream;

cooling the second bottoms stream in a heat exchanger to provide a cooled second bottoms stream; and removing the cooled vapor stream from an outlet of the contact cooler; wherein the first quench oil and second quench oil each comprise a hydrocarbon chosen to minimize vaporization of the first and second quench oils during the quench process, and wherein the first and second contact zones each comprise a packed bed.

9. The process of claim 8, further comprising:

passing the cooled vapor stream through a mesh blanket before removing the cooled vapor stream from the contact cooler.

10. The process of claim 8, further comprising:

returning at least a portion of the cooled first bottoms stream to the contact cooler to provide at least a portion of the first quench liquid; and returning at least a portion of the cooled second bottoms stream to the contact cooler to provide at least a portion of the second quench liquid.

11. The process of claim 8, wherein the first quench liquid and the second quench liquid each comprise at least one $C_{10}+$ hydrocarbon.

12. The process of claim 8, wherein the first bottoms stream is cooled by indirect heat exchange with water.

13. The process of claim 8, wherein the second bottoms stream is cooled by indirect heat exchange with water.

14. The process of claim 8, wherein the first and second contact zones each comprise a packed bed.

15. The process of claim 8, wherein the contact cooler has a first pressure at the inlet and a second pressure at the outlet, and difference between the first pressure and the second pressure is from about 0.5 psi to about 1.0 psi.

* * * * *